United States Patent [19]

Takeuchi et al.

[11] Patent Number: 5,126,327

[45] Date of Patent: Jun. 30, 1992

[54] MELANOCYTE-STIMULATING HORMONE INHIBITOR AND EXTERNAL PREPARATION CONTAINING THE SAME

[75] Inventors: Takuji Takeuchi; Chikara Sato, both of Sendai; Kenkichi Oba, Funabashi; Keikichi Sugiyama, Kanagawa, all of Japan

[73] Assignee: Lion Corporation, Tokyo, Japan

[21] Appl. No.: 497,191

[22] Filed: Mar. 22, 1990

[30] Foreign Application Priority Data

Mar. 23, 1989 [JP] Japan ................................ 1-71215
Apr. 13, 1989 [JP] Japan ................................ 1-93643

[51] Int. Cl.⁵ .................... A61K 37/02; C07K 5/00
[52] U.S. Cl. .................................. 514/18; 514/17; 514/16; 530/330; 530/329
[58] Field of Search ............ 530/333, 330, 329, 328, 530/327, 326, 325, 324; 514/12, 13, 14, 15, 16, 17, 18

[56] References Cited

U.S. PATENT DOCUMENTS 4,866,038 9/1989 Hruby et al. ..................... 514/14

FOREIGN PATENT DOCUMENTS 0292291 11/1988 European Pat. Off. .

OTHER PUBLICATIONS

Hawgood et al., Proc. Natl. Acad. Sci., vol. 84, pp. 66-70, (1987).
Chin et al., Nature, vol. 308, Apr. 12, 1984, pp. 613-617. Nucleotide sequence of 3-hydroxy-3-methylglutaryl CoA reductase.
Sawyer et al., J. Med. Chem., 25, 1982, pp. 1022-1027, Comparative Biological Activity of Highly Potent Active Site Analogue.
Wu et al., Nucleic Acid Research, 10(13), 1982, pp. 3831-3843.
Nucleotide Sequence of a Chromosomal Rearranged λ₂ immunoglobal.
Cashmore et al., Proc. Natl. Acad. Sci U.S.A., 81, May 1984 pp. 2960-2964.
Structure and Expression of a Pea Nucleargene Encoding a Chlorophy II.
Kameyama et al., "Expression of melanocyte stimulating hormone receptors correlates with mamalian pigmentation, and can be modulated by interferons", pp. 35-44, vol. 137, No. 1, 1988.
Hadley et al., "Biomedical Applications of Synthetic Melanotropins", *Pigment Cell Research*, Supplement 1 (1988), pp. 69-78.

*Primary Examiner*—Lester L. Lee
*Assistant Examiner*—A. M. Davenport
*Attorney, Agent, or Firm*—Burns, Doane, Swecker & Mathis

[57] ABSTRACT

A melanocyte-stimulating hormone inhibitor has an amino acid sequence represented by the following formula [I], [II] or [III] in the molecule:

—His—Ser—Arg—Trp— [I]

—Trp—Arg—Ser—His— [II]

—Leu—Ala—Cys—Ala—Arg— [III]

wherein His, Ser, Arg, Trp, Leu, Ala and Cys represent L— or D-histidine, serine, arginine, tryptophan, leucine, alanine and cysteine residues, respectively. The melanocyte-stimulating hormone inhibitor and an external preparation to be applied to the skin which contains the inhibitor prevent or cure the symptoms of chloasmata and freckles caused by an excess production of melanin by enhanced melanocyte function.

25 Claims, No Drawings

MELANOCYTE-STIMULATING HORMONE INHIBITOR AND EXTERNAL PREPARATION CONTAINING THE SAME

BACKGROUND OF THE INVENTION

The present invention provides novel compounds having an effect of inhibiting (antagonizing) the action of a melanocyte-stimulating hormone (melanotropin; hereinafter referred to as MSH) which activates function of the melanocytes, melanin producing cells in vivo. The present invention also relates to an external preparation to be applied to the skin which is capable of preventing or relieving the symptoms of chloasmata or freckles caused by, for example, an excess production of melanin by enhanced melanocyte function.

MSH is a peptide hormone contained in various vertebrate animals, and $\alpha$-, $\beta$- and $\gamma$-MSH have been known. It is known that they interact with a receptor on the melanocyte surface to successively activate adenylate cyclase and tyrosinase, and to accelerate melanine production. Among them, the effect of $\alpha$-MSH is particularly strong.

Various processes for inhibiting the function of melanocytes were proposed heretofore. They include, for example, a process wherein an inhibitor which reacts on the tyrosinase in the melanocytes is used. Kojic acid is practically used as the inhibitor as described in Japanese Patent Unexamined Published Application (hereinafter referred to as as 'J.P. KOKAI') Nos. 53-3538, 53-6432 and 53-18739. However, the conventional processes are not necessarily satisfactory from the viewpoints of effect and safety. Further the use of a substance which inhibits the effect per se of the melanocyte-stimulating hormone has scarcely been reported heretofore.

SUMMARY OF THE INVENTION

The primary object of the present invention is to provide an MSH inhibitor having high safety and excellent effect of inhibiting the functions of melanocyte such as melanin production as well as an external preparation containing the same to be applied to the skin.

This and other objects will be clear from the following description.

After synthesizing various peptides and investigating the relationship between the structure and the function thereof, the inventors have found that a peptide having a particular structure has an affinity for the receptor of the melanocytes and antagonizes MSH to specifically inhibit the melanin production of the melanocytes, or that such a peptide has an affinity for MSH per se and, as a result, it inhibits the function of MSH to specifically inhibit the melanin production of the melanocytes and that the above-described problems can be effectively solved by incorporating the peptide into an ordinary base of a cosmetic or medicine. The present invention has been completed on the basis of these findings.

The present invention provides a melanocyte-stimulating hormone inhibitor having an amino acid sequence represented by the following formula [I], [II], or [III] in the molecule:

-His-Ser-Arg-Trp-          [I]

-Trp-Arg-Ser-His-          [II]

-Leu-Ala-Cys-Ala-Arg-          [III]

wherein His, Ser, Arg, Trp, Leu, Ala and Cys represent L- or D-histidine, serine, arginine, tryptophan, leucine, alanine and cysteine residues, respectively.

DESCRIPTION OF THE PREFERRED EMBODIMENTS

The peptides represented by the above formulae [I] and [II] have an affinity for melanocyte receptor and antagonize MSH.

Any compounds having an amino acid sequence represented by the above formula [I] or [II] in the molecule can be used in the present invention. Among them, peptides of the following general formula [IV] or [V] are preferred:

X-His-Ser-Arg-Trp-Y          [IV]

P-Trp-Arg-Ser-His-Q          [V]

wherein His, Ser, Arg and Trp are as defined in the above formulae [I] and [II], His, Arg and Trp are preferably L-His, L-Arg and L-Trp residues, respectively, X and P each represent a hydrogen, acyl group, amino acid residue or acylated derivative thereof, peptide residue having 2 to 40, preferably 2 to 20 amino acid residues or acylated derivative thereof, X and P are preferably an acyl group, acylated amino acid residue or acylated peptide residue, the acyl group and acylated groups have 1 to 12, preferably 1 to 6 carbon atoms, Y and Q each represent a hydroxyl group, amino group, amino acid residue or amidated derivative thereof, peptide residue having 2 to 40, preferably 2 to 20 amino acid residues or amidated derivative thereof, and Y and Q are preferably an amino group, amidated amino acid residue or amidated peptide residue.

Various combinations of the amino acid residues and peptide residues of X, Y, P and Q can be used so far as they do not inhibit the function of antagonizing MSH. The peptide residues are preferably physiologically inert. As for the stereostructure of each amino acid residue, it may be either L- or D-type. Those derived from artificial amino acids such as norleucine and norvaline are also usable. X, Y, P and Q may have a sugar chain.

The stability of the compound of the present invention to various proteases can be improved to exhibit the MSH-inhibition effect by employing a D-amino acid residue or synthetic amino acid residue as X, Y, P or Q.

X, Y, P and Q may further contain various substituents such as hydroxyl group and halogens.

The amino acid sequence of X, Y, P or Q preferably contains -Ser-Tyr-Ser- in order to exhibit a high affinity for the ligand. The stability and physiological activity of the product can be improved by incorporating biotin or the like into the above-described sequence of the three amino acids.

The molecular weight of the compound of the general formula [IV] [V] comprising at least four amino acid residues as shown above is 584 to 10,000, preferably 600 to 6,000 and particularly preferably 600 to 3000. The number of the amino acid residues is 4 to 84, preferably 4 to 44 and particularly preferably 4 to 24.

The peptides of the formula [III] have an affinity for MSH per se and, therefore, they are capable of inhibiting the effect of MSH like the peptides of the formula [I] or [II].

Any compounds having the amino acid sequence as shown by the formula [III] can be used in the present invention. Among them, peptides represented by the following general formula [VI] are preferred:

$$X_1\text{-Leu-Ala-Cys-Ala-Arg-}Y_1 \qquad [VI]$$

wherein $X_1$ represents a hydrogen, acyl group, amino acid residue, peptide residue having 2 to 40, preferably 2 to 20 amino acid residues or acylated derivative thereof, and $X_1$ is preferably a hydrogen, acyl group, peptide residue having an amino acid sequence of -Ile-Leu or -Leu-His-Ala-Leu-Gln-Leu-Leu-Leu-Ile-Leu or acylated derivative thereof, the acyl group or acylated derivative has 1 to 12 carbon atoms, preferably 1 to 6 carbon atoms; and $Y_1$ represents a hydroxyl group, amino group, amino acid residue, amidated derivative thereof, peptide residue having 2 to 36, preferably 2 to 16 peptide residues or amidated derivative thereof and $Y_1$ is preferably a hydroxyl group, amino group, peptide residue having an amino acid sequence of Ile-Ser-Pro-Gly-Arg-Arg-or amidated derivative thereof.

Various combinations of the amino acid residues and peptide residues of $X_1$ and $Y_1$ can be employed so far as they do not inhibit the MSH-inhibiting function. The peptide residue is preferably physiologically inert. $X_1$ and $Y_1$ may have a sugar chain.

The molecular weight of the compound of the formula [VI] comprising at least five amino acid residues as shown above is 532 to 10,000, preferably 532 to 6,000 and particularly preferably 532 to 4,000. The number of the amino acid residues is 5 to 81, preferably 5 to 41 and particularly preferably 5 to 31.

Examples of the compounds of the general formulae [IV] and [V] are shown in Table 1 and those of the compounds of the general formula [VI] are shown in Table 2.

In tables 1 and 2, the amino acid residues constituting the peptide are shown by abbreviations according to IUPAC, L-amino acids are shown without "L-" and D-amino acids are shown with "D" such as "D-Ser". Synthetic amino acid residues, i.e., norleucine and norvaline residues, are shown as Nle and Nva, respectively. In line with the ordinary mode of expression, the amino acid terminal (N-terminal) of the peptide is shown on the left and the carboxyl terminal (C-terminal) thereof is shown on the right of this specification. Ac represents acetyl group and Bu represents butyryl group (hereinafter the same). In Table 2, when N-terminal of $X_1$ is hydrogen and C-terminal of $Y_1$ is hydroxyl group, H- or -OH is not shown.

TABLE 1

| No. | Compound of formula [IV] Sequence of essential amino acids | X | Y |
|---|---|---|---|
| 1 | H—His—Ser—Arg—Trp—OH | | |
| 2 | Ac—His—Ser—Arg—Trp—NH₂ | | |
| 3 | Ac—His—D—Ser—Arg—Trp—NH₂ | | |
| 4 | H—Glu—His—Ser—Arg—Trp—Gly—OH | | |
| 5 | Ac—Glu—His—Ser—Arg—Trp—Gly—NH₂ | | |
| 6 | Ac—Glu—His—D—Ser—Arg—Trp—Gly—NH₂ | | |
| 7 | H—Met—Glu—His—Ser—Arg—Trp—Gly—OH | | |
| 8 | Ac—Met—Glu—His—Ser—Arg—Trp—Gly—NH₂ | | |
| 9 | Ac—Met—Glu—His—D—Ser—Arg—Trp—Gly—NH₂ | | |
| 10 | H—Nle—Glu—His—Ser—Arg—Trp—Gly—OH | | |
| 11 | Ac—Nle—Glu—His—Ser—Arg—Trp—Gly—NH₂ | | |
| 12 | Ac—Nle—Glu—His—D—Ser—Arg—Trp—Gly—NH₂ | | |
| 13 | H—Met—Glu—His—Ser—Arg—Trp—Gly—Lys—OH | | |
| 14 | Ac—Met—Glu—His—Ser—Arg—Trp—Gly—Lys—NH₂ | | |
| 15 | Ac—Met—Glu—His—D—Ser—Arg—Trp—Gly—Lys—NH₂ | | |
| 16 | H—Nle—Glu—His—Ser—Arg—Trp—Gly—Lys—OH | | |
| 17 | Ac—Nle—Glu—His—Ser—Arg—Trp—Gly—Lys—NH₂ | | |
| 18 | Ac—Nle—Glu—His—D—Ser—Arg—Trp—Gly—Lys—NH₂ | | |
| 19 | H—Ser—Met—Glu—His—Ser—Arg—Trp—Gly—Lys—Pro—OH | | |
| 20 | H—Ser—Met—Glu—His—Ser—Arg—Trp—Gly—Lys—Pro—NH₂ | | |
| 21 | Ac—Ser—Met—Glu—His—Ser—Arg—Trp—Gly—Lys—Pro—NH₂ | | |
| 22 | H—Ser—Nle—Glu—His—Ser—Arg—Trp—Gly—Lys—Pro—OH | | |
| 23 | Ac—Ser—Nle—Glu—His—Ser—Arg—Trp—Gly—Lys—Pro—NH₂ | | |
| 24 | Ac—Ser—Nle—Glu—His—D—Ser—Arg—Trp—Gly—Lys—Pro—NH₂ | | |
| 25 | H—Ser—Tyr—Ser—Met—Glu—His—Ser—Arg—Trp—Gly—Lys—Pro—OH | | |
| 26 | Ac—Ser—Tyr—Ser—Met—Glu—His—Ser—Arg—Trp—Gly—Lys—Pro—NH₂ | | |
| 27 | Ac—Ser—Tyr—Ser—Met—Glu—His—D—Ser—Arg—Trp—Gly—Lys—Pro—NH₂ | | |
| 28 | H—Ser—Tyr—Ser—Nle—Glu—His—Ser—Arg—Trp—Gly—Lys—Pro—OH | | |
| 29 | Ac—Ser—Tyr—Ser—Nle—Glu—His—Ser—Arg—Trp—Gly—Lys—Pro—NH₂ | | |
| 30 | Ac—Ser—Tyr—Ser—Nle—Glu—His—D—Ser—Arg—Trp—Gly—Lys—Pro—NH₂ | | |
| 31 | H—D—Ser—Tyr—Ser—Met—Glu—His—Ser—Arg—Trp—Gly—Lys—Pro—OH | | |
| 32 | Ac—D—Ser—Tyr—Ser—Met—Glu—His—Ser—Arg—Trp—Gly—Lys—Pro—NH₂ | | |
| 33 | Ac—D—Ser—Tyr—Ser—Met—Glu—His—D—Ser—Arg—Trp—Gly—Lys—Pro—NH₂ | | |
| 34 | H—D—Ser—Tyr—Ser—Nle—Glu—His—Ser—Arg—Trp—Gly—Lys—Pro—OH | | |
| 35 | Ac—D—Ser—Tyr—Ser—Nle—Glu—His—Ser—Arg—Trp—Gly—Lys—Pro—NH₂ | | |
| 36 | Ac—D—Ser—Tyr—Ser—Nle—Glu—His—D—Ser—Arg—Trp—Gly—Lys—Pro—NH₂ | | |
| 37 | H—Ser—Tyr—Ser—Met—Glu—His—Ser—Arg—Trp—Gly—Lys—Pro—Val—OH | | |
| 38 | Ac—Ser—Tyr—Ser—Met—Glu—His—Ser—Arg—Trp—Gly—Lys—Pro—Val—OH | | |
| 39 | H—Ser—Tyr—Ser—Met—Glu—His—Ser—Arg—Trp—Gly—Lys—Pro—Val—NH₂ | | |
| 40 | Ac—Ser—Tyr—Ser—Met—Glu—His—Ser—Arg—Trp—Gly—Lys—Pro—Val—NH₂ | | |
| 41 | Ac—Ser—Tyr—Ser—Met—Glu—His—D—Ser—Arg—Trp—Gly—Lys—Pro—Val—NH₂ | | |
| 42 | Bu—Ser—Tyr—Ser—Met—Glu—His—Ser—Arg—Trp—Gly—Lys—Pro—Val—NH₂ | | |
| 43 | H—Ser—Tyr—Ser—Nle—Glu—His—Ser—Arg—Trp—Gly—Lys—Pro—Val—OH | | |
| 44 | Ac—Ser—Tyr—Ser—Nle—Glu—His—Ser—Arg—Trp—Gly—Lys—Pro—Val—NH₂ | | |
| 45 | H—Ser—Tyr—Ser—Nle—Glu—His—Ser—Arg—Trp—Gly—Lys—Pro—Val—NH₂ | | |
| 46 | Ac—Ser—Tyr—Ser—Nle—Glu—His—Ser—Arg—Trp—Gly—Lys—Pro—Val—NH₂ | | |
| 47 | Ac—Ser—Tyr—Ser—Nle—Glu—His—D—Ser—Arg—Trp—Gly—Lys—Pro—Val—NH₂ | | |
| 48 | Bu—Ser—Tyr—Ser—Nle—Glu—His—Ser—Arg—Trp—Gly—Lys—Pro—Val—NH₂ | | |
| 49 | H—D—Ser—Tyr—Ser—Met—Glu—His—Ser—Arg—Trp—Gly—Lys—Pro—Val—OH | | |
| 50 | Ac—D—Ser—Tyr—Ser—Met—Glu—His—Ser—Arg—Trp—Gly—Lys—Pro—Val—NH₂ | | |
| 51 | Ac—D—Ser—Tyr—Ser—Met—Glu—His—D—Ser—Arg—Trp—Gly—Lys—Pro—Val—NH₂ | | |

TABLE 1-continued

| No. | Compound of formula [V] Sequence of essential amino acids |
|---|---|
| 52 | H—Ser—Tyr—Ser—Met—Glu—His—Ser—Arg—Trp—Gly—Lys—Pro—Nva—OH |
| 53 | Ac—Ser—Tyr—Ser—Met—Glu—His—Ser—Arg—Trp—Gly—Lys—Pro—Nva—NH₂ |
| 54 | Ac—Ser—Tyr—Ser—Met—Glu—His—D—Ser—Arg—Trp—Gly—Lys—Pro—Nva—NH₂ |
| 55 | H—Ser—Tyr—Ser—Met—Glu—His—Ser—Arg—Trp—Gly—Lys—Pro—Met—OH |
| 56 | Ac—Ser—Tyr—Ser—Met—Glu—His—Ser—Arg—Trp—Gly—Lys—Pro—Met—NH₂ |
| 57 | Ac—Ser—Tyr—Ser—Met—Glu—His—D—Ser—Arg—Trp—Gly—Lys—Pro—Met—NH₂ |
| 58 | H—D—Ser—Tyr—Ser—Nle—Glu—His—Ser—Arg—Trp—Gly—Lys—Pro—Val—OH |
| 59 | Ac—D—Ser—Tyr—Ser—Nle—Glu—His—Ser—Arg—Trp—Gly—Lys—Pro—Val—NH₂ |
| 60 | Ac—D—Ser—Tyr—Ser—Nle—Glu—His—D—Ser—Arg—Trp—Gly—Lys—Pro—Val—NH₂ |
| 61 | H—Ser—Tyr—Ser—Phe—Met—Glu—His—Ser—Arg—Trp—Gly—Lys—Pro—Val—OH |
| 62 | Ac—Ser—Tyr—Ser—Phe—Met—Glu—His—Ser—Arg—Trp—Gly—Lys—Pro—Val—NH₂ |
| 63 | Ac—Ser—Tyr—Ser—Phe—Met—Glu—His—D—Ser—Arg—Trp—Gly—Lys—Pro—Val—NH₂ |

| No. | Compound of formula [V] | | |
|---|---|---|---|
| | P | Sequence of essential amino acids | Q |
| 64 | | H—Trp—Arg—Ser—His—OH | |
| 65 | | Ac—Trp—Arg—Ser—His—NH₂ | |
| 66 | | Ac—Trp—Arg—D—Ser—His—NH₂ | |
| 67 | | H—Cys—Trp—Arg—Ser—His—Gln—OH | |
| 68 | | Ac—Cys—Trp—Arg—Ser—His—Gln—NH₂ | |
| 69 | | Ac—Cys—Trp—Arg—D—Ser—His—Gln—NH₂ | |
| 70 | | H—Cys—Trp—Arg—Ser—His—Gln—Pro—OH | |
| 71 | | Ac—Cys—Trp—Arg—Ser—His—Gln—Pro—NH₂ | |
| 72 | | Ac—Cys—Trp—Arg—D—Ser—His—Gln—Pro—NH₂ | |
| 73 | | H—Cys—Cys—Trp—Arg—Ser—His—Gln—Pro—OH | |
| 74 | | Ac—Cys—Cys—Trp—Arg—Ser—His—Gln—Pro—NH₂ | |
| 75 | | Ac—Cys—Cys—Trp—Arg—D—Ser—His—Gln—Pro—NH₂ | |
| 76 | | H—His—Cys—Cys—Trp—Arg—Ser—His—Gln—Pro—Ala—OH | |
| 77 | | Ac—His—Cys—Cys—Trp—Arg—Ser—His—Gln—Pro—Ala—NH₂ | |
| 78 | | Ac—His—Cys—Cys—Trp—Arg—D—Ser—His—Gln—Pro—Ala—NH₂ | |
| 79 | | H—His—Cys—Cys—Trp—Arg—Ser—His—Gln—Pro—Arg—Pro—OH | |
| 80 | | Ac—His—Cys—Cys—Trp—Arg—Ser—His—Gln—Pro—Arg—Pro—NH₂ | |
| 81 | | Ac—His—Cys—Cys—Trp—Arg—D—Ser—His—Gln—Pro—Arg—Pro—NH₂ | |
| 82 | | H—Cys—His—Cys—Cys—Trp—Arg—Ser—His—Gln—Pro—Ala—Arg—Pro—OH | |
| 83 | | Ac—Cys—His—Cys—Cys—Trp—Arg—Ser—His—Gln—Pro—Ala—Arg—Pro—NH₂ | |
| 84 | | Ac—Cys—His—Cys—Cys—Trp—Arg—D—Ser—His—Gln—Pro—Ala—Arg—Pro—NH₂ | |
| 85 | | Ac—Cys—His—Cys—Cys—Trp—Arg—Ser—His—Gln—Pro—Ala—Arg—Pro—NH₂ | |
| 86 | | Ac—Cys—His—Cys—Cys—Trp—Arg—D—Ser—His—Gln—Pro—Ala—Arg—Pro—NH₂ | |
| 87 | | Bu—Cys—His—Cys—Cys—Trp—Arg—Ser—His—Gln—Pro—Ala—Arg—Pro—NH₂ | |
| 88 | H—Leu—Met—Leu—Gly—Pro—Leu—Gly—Pro—Leu—Gly—Pro—Leu—Gly—Pro—Ala—Arg—Pro—Phe—Leu—Leu—Gly—Leu—OH | | |
| 89 | Ac—Leu—Met—Leu—Gly—Pro—Leu—Gly—Pro—Leu—Gly—Pro—Leu—Gly—Pro—Ala—Arg—Pro—Phe—Leu—Leu—Gly—Leu—OH | | |
| 90 | H—Leu—Met—Leu—Gly—Pro—Leu—Gly—Pro—Leu—Gly—Pro—Leu—Gly—Pro—Ala—Arg—Pro—Phe—Leu—Leu—Gly—Leu—NH₂ | | |
| 91 | Ac—Leu—Met—Leu—Gly—Pro—Leu—Gly—Pro—Leu—Gly—Pro—Leu—Gly—Pro—Ala—Arg—Pro—Phe—Leu—Leu—Gly—Leu—NH₂ | | |
| 92 | Ac—Leu—Met—Leu—Gly—Pro—Leu—Gly—Pro—Leu—Cys—His—Cys—Cys—Trp—Arg—D—Ser—His—Gln—Pro—Leu—Gly—Leu—NH | | |
| | Arg—Pro—Phe—Leu—Cys—Cys—His—Cys—Cys—Trp—Arg—Ser—His—Gln—Pro—Ala— | | |
| 93 | Bu—Leu—Met—Leu—Gly—Pro—Leu—Cys—His—Cys—Cys—Trp—Arg—Ser—His—Gln—Pro—Ala— | | |
| | Arg—Pro—Phe—Leu—Gly—Leu—NH₂ | | |

TABLE 2

| No. | X₁ | Compound of formula [VI] Sequence of essential amino acids | Y₁ |
|---|---|---|---|
| 101 | | Leu—Ala—Cys—Ala—Arg | |
| 102 | | Ac—Leu—Ala—Cys—Ala—Arg—NH₂ | |
| 103 | | Leu—Ala—Cys—Ala—Arg—Ile | |
| 104 | | Ac—Leu—Ala—Cys—Ala—Arg—Ile—NH₂ | |
| 105 | | Leu—Ala—Cys—Ala—Arg—Ile—Ser | |
| 106 | | Ac—Leu—Ala—Cys—Ala—Arg—Ile—Ser—NH₂ | |
| 107 | | Leu—Ala—Cys—Ala—Arg—Ile—Ser—Pro | |
| 108 | | Ac—Leu—Ala—Cys—Ala—Arg—Ile—Ser—Pro—NH₂ | |
| 109 | | Leu—Ala—Cys—Ala—Arg—Ile—Ser—Pro—Gly | |
| 110 | | Ac—Leu—Ala—Cys—Ala—Arg—Ile—Ser—Pro—Gly—NH₂ | |
| 111 | | Leu—Leu—Ala—Cys—Ala—Arg—Ile—Ser—Pro—Gly—Arg | |
| 112 | | Ac—Leu—Leu—Ala—Cys—Ala—Arg—Ile—Ser—Pro—Gly—Arg—NH₂ | |
| 113 | | Ile—Leu—Leu—Ala—Cys—Ala—Arg—Ile—Ser—Pro—Gly—Arg—Arg | |
| 114 | | Ac—Ile—Leu—Leu—Ala—Cys—Ala—Arg—Ile—Ser—Pro—Gly—Arg—Arg—NH₂ | |
| 115 | | Ile—Leu—Leu—Ala—Cys—Ala—Arg—Ile—Ser—Pro—Gly—Arg—Arg | |
| 116 | | Ac—Ile—Leu—Leu—Ala—Cys—Ala—Arg—Ile—Ser—Pro—Gly—Arg—Arg—NH₂ | |
| 117 | | Bu—Ile—Leu—Leu—Ala—Cys—Ala—Arg—Ile—Ser—Pro—Gly—Arg—Arg—NH₂ | |
| 118 | | Leu—Ile—Leu—Leu—Ala—Cys—Ala—Arg—Ile—Ser—Pro—Gly—Arg—Arg | |
| 119 | | Ac—Leu—Ile—Leu—Leu—Ala—Cys—Ala—Arg—Ile—Ser—Pro—Gly—Arg—Arg—NH₂ | |
| 120 | | Leu—Leu—Ile—Leu—Leu—Ala—Cys—Ala—Arg—Ile—Ser—Pro—Gly—Arg—Arg | |
| 121 | | Ac—Leu—Leu—Ile—Leu—Leu—Ala—Cys—Ala—Arg—Ile—Ser—Pro—Gly—Arg—Arg—NH₂ | |
| 122 | | Leu—Leu—Leu—Ile—Leu—Leu—Ala—Cys—Ala—Arg—Ile—Ser—Pro—Gly—Arg—Arg | |
| 123 | | Ac—Leu—Leu—Leu—Ile—Leu—Leu—Ala—Cys—Ala—Arg—Ile—Ser—Pro—Gly—Arg—Arg—NH₂ | |
| 124 | | Gln—Leu—Leu—Leu—Ile—Leu—Leu—Ala—Cys—Ala—Arg—Ile—Ser—Pro—Gly—Arg—Arg | |
| 125 | | Ac—Gln—Leu—Leu—Leu—Ile—Leu—Leu—Ala—Cys—Ala—Arg—Ile—Ser—Pro—Gly—Arg—Arg—NH₂ | |
| 126 | | Leu—Gln—Leu—Leu—Leu—Ile—Leu—Leu—Ala—Cys—Ala—Arg—Ile—Ser—Pro—Gly—Arg—Arg | |
| 127 | | Ac—Leu—Gln—Leu—Leu—Leu—Ile—Leu—Leu—Ala—Cys—Ala—Arg—Ile—Ser—Pro—Gly—Arg—Arg—NH₂ | |
| 128 | | Ala—Leu—Gln—Leu—Leu—Leu—Ile—Leu—Leu—Ala—Cys—Ala—Arg—Ile—Ser—Pro—Gly—Arg—Arg | |
| 129 | | Ac—Ala—Leu—Gln—Leu—Leu—Leu—Ile—Leu—Leu—Ala—Cys—Ala—Arg—Ile—Ser—Pro—Gly—Arg—Arg—NH₂ | |
| 130 | | His—Ala—Leu—Gln—Leu—Leu—Leu—Ile—Leu—Leu—Ala—Cys—Ala—Arg—Ile—Ser—Pro—Gly—Arg—Arg | |
| 131 | | Ac—His—Ala—Leu—Gln—Leu—Leu—Leu—Ile—Leu—Leu—Ala—Cys—Ala—Arg—Ile—Ser—Pro—Gly—Arg—Arg—NH₂ | |
| 132 | | Leu—His—Ala—Leu—Gln—Leu—Leu—Leu—Ile—Leu—Leu—Ala—Cys—Ala—Arg—Ile—Ser—Pro—Gly—Arg—Arg | |
| 133 | | Ac—Leu—His—Ala—Leu—Gln—Leu—Leu—Leu—Ile—Leu—Leu—Ala—Cys—Ala—Arg—Ile—Ser—Pro—Gly—Arg—Arg—NH₂ | |
| 134 | | Leu—Leu—His—Ala—Leu—Gln—Leu—Leu—Leu—Ile—Leu—Leu—Ala—Cys—Ala—Arg—Ile—Ser—Pro—Gly—Arg—Arg | |
| 135 | | Ac—Leu—His—Ala—Leu—Gln—Leu—Leu—Leu—Ile—Leu—Leu—Ala—Cys—Ala—Arg—Ile—Ser—Pro—Gly—Arg—Arg—NH₂ | |
| 136 | | Bu—Leu—His—Ala—Leu—Gln—Leu—Leu—Leu—Ile—Leu—Leu—Ala—Cys—Ala—Arg—Ile—Ser—Pro—Gly—Arg—Arg—NH₂ | |
| 137 | Leu—Asn—His—Leu—Gly—Leu—Asn—His—Ala—Leu—Gln—Leu—Leu—Leu—Ile—Leu—Leu—Ala—Cys—Ala—Arg—Ile—Ser—Pro—Gly— | | |
| 138 | Ac—Leu—Asn—His—Leu—Gly—Leu—Asn—His—Ala—Leu—Gln—Leu—Leu—Leu—Ile—Leu—Leu—Ala—Cys—Ala—Arg—Ile—Ser—Pro—Cys— | | |
| 139 | Gln—Phe—Leu—Leu—Gln—Leu—Asn—His—Leu—Gly—Leu—Asn—His—Ala—Leu—Gln—Leu—Leu—Leu—Ile—Leu—Leu—Ala—Cys—Ala—Arg—Ile—Ser—Pro—Gly— | Arg—Arg—Ala—Cys—Arg—Pro—His—Ala—Val—Leu | |
| 140 | Ac—Gln—Phe—Leu—Leu—Ala—Leu—Gln—Leu—Asn—His—Leu—Gly—Leu—Asn—His—Ala—Leu—Gln—Leu—Leu—Leu—Ile—Leu—Leu— | | |
| | Ile—Leu—Leu—Ala—Cys—Ala—Arg—Ile—Ser—Pro—Gly—Arg—Arg—Ala—Cys—Arg—Pro—His—Ala—Val—Leu—NH₂ | | |

The MSH inhibitor of the present invention can be produced by a liquid phase method or solid phase method usually employed for synthesizing peptides.

In the liquid phase method, an amino group of a starting amino acid is protected with benzyloxycarbonyl group, t-butoxycarbonyl group or the like and a carboxyl group of the other starting amino acid or peptide is protected with a benzyl ester or the like and they are coupled together in the presence of DCC (N,N'-dicyclohexyl carbodiimide) or the like. This procedure is repeated and then the protective groups are removed and the product is purified to obtain the compound of the present invention. In the solid phase method, an amino acid at the C-terminal is coupled with a cross-linked polystyrene resin and then t-butoxycarbonyl amino acid is coupled with the N-terminal one by one. After completion of the reaction, the product is removed from the resin, the protective group is removed and the product is purified to obtain the compound of the present invention.

The intended product can be produced also by incorporating DNA which codes the effective component of the present invention into microorganisms such as *Escherichia coli*.

The MSH-inhibitor of the present invention is in a white powder form at ambient temperature.

The MSH-inhibitor of the present invention is effective for preventing or curing symptoms caused by epidermal or dermal chloasmata, freckles and birthmarks due to excess production of the melanin or for inhibiting abnormal growth of melanoma, i.e. cancered melanocytes. By suitably managing the administration method of the MSH-inhibitor of the present invention or suitably controlling the amount thereof, the color of the skin or hair can be changed and, therefore, it is usable also as a whitening agent. Recently, it is known that MSH has various physiological functions in vivo such as fat production, sebum production, pheromone production, steroid production, aldosterone biosynthesis and action as a neuro-hormone in the brain. The active component of the present invention is capable of controlling the various effects of MSH in these cells and tissues.

Thus the MSH-inhibitor of the present invention can be applied to not only human beings but also animals having MSH in their bodies such as mammals, e.g. dogs and cats, reptiles, batrachians and fishes. As a matter of course, the MSH-inhibitor of the present invention is usable as a diagnostic agent or biochemical reagent in vitro.

In applying the MSH-inhibitor of the present invention in vivo, it can be used in various forms depending on the animal to which it is to be applied, the cells, the location of the tissue, easiness of arrival at the target region and ease of application. Namely, it can be incorporated into a cosmetic base or medicine base to be used as an external preparation to be applied to the skin, oral preparation or injection. The concentration of the active compound of the present invention in these preparations is not limited. The concentration which varies depending on the purpose, form and frequency of the application is usually about 0.0000000001 to 1% (by weight; the same shall apply hereinafter), preferably 0.00000001 to 0.1%. In this connection, it is preferable to contain balance of water as an inert carrier, more preferably 1 to 99 wt. % of water.

Among the preparations containing the MSH-inhibitor of the present invention, the external preparation to be applied to the skin can contain, in addition to the above-described indispensable component, various materials usually contained in external preparations such as a surfactant, oil, alcohol, humectant, thickening agent, antiseptic, antioxidant, chelating agent, pH adjustor, perfume, colorant, U.V. ray absorber, U.V. ray scattering agent, vitamins, amino acids and water.

The surfactants include, for example, nonionic surfactants such as lipophilic glyceryl monostearate, self-emulsifying glyceryl monostearate, polyglyceryl monostearate, sorbitan monooleate, polyethyleneglycol monostearate, polyoxyethylene sorbitan monooleate, polyoxyethylene cetylether, polyoxyethylene sterol, polyoxyethylene lanolin, polyoxyethylene beeswax and polyoxyethylene hydrogenated castor oil; anionic surfactants such as sodium stearate, potassium palmitate, sodium cetyl sulfate, sodium lauryl phosphate, triethanolamine palmitate, sodium polyoxyethylene lauryl phosphate and sodium N-acylglutamate; cationic surfactants such as stearyldimethylbenzylammonium chloride and stearyltrimethylammonium chloride; and amphoteric surfactants such as alkyl-aminoethylglycine hydrochloride solution and lecithin.

The oils include, for example, vegetable oils and fats such as castor oil, olive oil, cacao butter, tsubaki oil, cocounut oil, Japan wax, Jojoba oil, grape seed oil and avocado oil; animal oils and fats such as mink oil and egg yolk oil; waxes such as beeswax, spermaceti, lanolin, carnauba wax and candelilla wax; hydrocarbons such as liquid paraffin, squalane, microcrystalline wax, ceresine wax, paraffin wax and vaseline; natural and synthetic fatty acids such as lauric acid, myristic acid, stearic acid, oleic acid, isostearic acid and behenic acid; natural and synthetic higher alcohols such as cetanol, stearyl alcohol, hexyldecanol, octyldodecanol and lauryl alcohol; and esters such as isopropyl myristate, isopropyl palmitate, octyldodecyl myristate, octyldodecyl oleate and cholesterol oleate.

The humectants include, for example, polyhydric alcohols such as glycerol, propylene glycol, 1,3-butylene glycol, sorbitol, polyglycerol, polyethylene glycol and dipropylene glycol; NMF components such as amino acids, sodium lactate and sodium pyrrolidone carboxylate; and water-soluble high-molecular substances such as hyaluronic acid, collagen, mucopolysaccharides and chondroitin sulfate.

The thickening agents include natural high molecular substances such as sodium alginate, xanthane gum, aluminum silicate, quince seed extract, tragacanth gum and starches; semisynthetic high molecular substances such as methyl cellulose, hydroxyethyl cellulose, carboxymethyl cellulose, soluble starch and cationized cellulose; and synthetic high polymers such as carboxyvinyl polymer and polyvinyl alcohol.

The antiseptics include, for example, benzoates, salicylates, sorbates, dehydroacetates, p-hydroxybenzoic esters, 2,4,4'-trichloro-2'hydroxydiphenyl ether, 3,4,4'-trichlorocarbanilide, benzalkonium chloride, hinokitiol, resorcin and ethanol.

The antioxidants include, for example, dibutylhydroxytoluene, butylhydroxyanisole, propyl gallate and ascorbic acid. The chelating agents include, for example, disodium edetate, ethylenediaminetetraacetates, pyrophosphates, hexametaphosphates, citric acid, tartaric acid and gluconic acid. The pH adjustors include, for example, sodium hydroxide, triethanolamine, citric acid, sodium citrate, boric acid, borax and potassium hydrogenphosphate.

The U.V. ray absorbers and U.V. ray scattering agents include, for example, 2-hydroxy-4-methoxybenzophenone, octyl dimethyl p-aminobenzoate, ethyl hexyl-p-methoxycinnamate, titanium oxide, kaolin and talc.

The vitamins include, for example, vitamin A, vitamin B, vitamin C, vitamin D, vitamin E, vitamin F, vitamin K, vitamin P, vitamin U, carnitine, ferulic acid γ-oryzanol, α-lipoic acid, orotic acid and derivatives of them.

The amino acids include, for example, glycine, alanine, valine, leucine, isoleucine, serine, threonine, phenylalanine, tyrosine, tryptophan, cystine, cysteine, methionine, proline, hydroxyproline, aspartic acid, glutamic acid, arginine, histidine, lysine and derivatives of them.

The additives are not limited to those described above. By suitably combining the indispensable component with the additives, an external preparation to be appied to the skin which comprises 0.0000000001 to 1% of the indispensable component and, as additives, 0 to 80% of the oil, 0 to 12% (preferably 0.05 to 8%) of the surfactant, 1 to 15% of the humectant, the balance of purified water and a small amount of the antiseptic can be obtained. The preparation can be in various forms such as a cream, milky lotion, toilet water, beauty essence, pack, undermakeup, foundation, jelly and ointment.

Examples of the compositions to be used as cosmetics to be applied to the skin are as follows:

Skin Cream

A composition comprising 0.00000001 to 0.1% of the indispensable component, 20 to 70% of the oil, 2 to 7% of the surfactant, 1 to 10% of the humectant, the balance of purified water and small amounts of the antiseptic and perfume.

Milky Lotion

A composition comprising 0.00000001 to 0.1% of the indispensable component, 10 to 40% of the oil, 0 to 15% of the alcohol, 1 to 5% of the surfactant, 1 to 10% of the humectant, 0 to 2% of the thickening agent, the balance of purified water and small amounts of the antiseptic and perfume.

Toilet Water and Beauty Essence

A composition comprising 0.00000001 to 0.1% of the indispensable component, 5 to 20% of the alcohol, 0 to 2% of the surfactant, 2 to 8% of the humectant, 0 to 2% of the thickening agent, 0 to 0.5% of the antioxidant, 0 to 0.1% of the chelating agent, 0 to 0.2% of the pH adjustor, the balance of purified water, and small amounts of the antiseptic, colorant (if necessary) and perfume, and Pack A composition comprising 0.00000001 to 0.1% of the indispensable component, 2 to 10% of the alcohol, 2 to 10% of the humectant, 0 to 20% of an inorganic powder, 10 to 20% of a film-forming agent, the balance of purified water and small amounts of the antiseptic and perfume.

Examples of the compositions to be used as ointments are as follows:

Hydrophilic Ointment

A composition comprising 0.00000001 to 0.1% of the indispensable component, 40 to 60% of the oil, 1 to 12% of the surfactant, 8 to 15% of the humectant, the balance of purified water and a small amount of the antiseptic, and Oily Ointment A composition comprising 0.00000001 to 0.1% of the indispensable component, 95 to 99% of an oil and the balance of purified water.

The oral preparations containing the MSH inhibitor of the present invention include, for example, a solid preparation such as tablets comprising the indispensable component of the present invention and an excipient such as starch, glucose or lactose, or a liquid preparation comprising the indispensable component, a sugar, water and ethanol. In the oral administration, the amount of the indispensable component of the present invention is 10 to 10,000 μg/kg.

When the indispensable component of the present invention is used in the form of an injection, it is dissolved in a solvent such as water or physiological saline to form a solution to be used as an intracutaneous injection or intramuscular injection. In the injections, the amount of the indispensable component of the present invention is 1 μg/kg to 10,000 μg/kg.

Although the mechanism of the excellent effect of the active component of the present invention for inhibiting MSH has not fully been elucidated, it is supposed as follows:

M. E. Hadley et al. found that the minimum structure of MSH necessitated for activating the melanocytes is Ac-His-Phe-Arg-Trp-NH$_2$ [see Pigment Cell Research Supplement 1: 69–78 (1988)].

Since the MSH-inhibitors of the formulae [I] and [II] of the present invention have a structure similar to the amino acid sequence of the minimum structure in the molecule, it is supposed that the inhibitor has a strong affinity for the MSH receptor and, as a result, the bonding of MSH with the receptor is inhibited thereby to exhibit an excellent effect of inhibiting melanin formation.

One on the hand, the peptide of the formula [III] has the sequence of the five amino acid residues shown by the formula [III] in its molecule, which sequence is complementary to amino acid sequence having MSH activity and which sequence is considered to have a high structural affinity for MSH, so that the peptide preferentially bonds with MSH and, as a result, the bonding of MSH with the receptor is inhibited thereby to exhibit the excellent melanin production-inhibiting effect.

It was confirmed that the stability of this component in the external preparation is high and it has a high practical value.

The active component of the present invention is free from any problem such as irritation of the skin in the practical use.

According to the present invention, the function of the melanocytes is inhibited by the MSH-inhibiting (-antagonizing) effect and the symptoms caused by the exaggerated melanocyte function such as chloasmata or freckles essentially disappear. The present invention also provides a stable external preparation to be applied to the skin, oral preparation or injection having an excellent whitening effect.

The following examples will further illustrate the present invention.

EXAMPLE 1

Compound Nos. 40 and 85 in Table 1 which are active components of the present invention were synthesized by the solid phase method and purified as described below.

Val or Pro which was the amino acid at the C-terminal was coupled with a crosslinked polystyrene resin. Then amino acids having the amino group protected with t-butoxycarbonyl group were coupled with the N-terminal one by one. After all the amino acids had been coupled with the resin, the amino terminal was acetylated, the peptide having the protective group was removed from the resin, and the protective group was removed.

The unpurified compound thus obtained was purified according to liquid chromatography to obtain the effective components of the present invention (compound Nos. 40 and 85 in Table 1).

EXAMPLE 2

MSH-antagonizing effects of the compounds of the present invention obtained in Example 1 (compound Nos. 40 and 85 in Table 1) and compounds of the present invention synthesized in the same manner as that of Example 1 (compound Nos. 14 and 74 in Table 1) were examined as described below.

Skin grafts (about 1 mm × 1 mm) of yellow mice (C 57 BL/6J-A') (7.5 days after the birth) containing hair follicle melanocytes were cultured in Ham's F-12 culture medium at 37° C. for 2 days. The culture media used were: (i) Ham's F-12 medium containing α-MSH, (ii) that containing both α-MSH and the compound of the present invention, i.e., the compound of the present invention and the skin grafts had been incubated in a Ham's F-12 medium so as to interact the compounds with a receptor on the melanocyte surface of the skin and then the resultant was contacted with α-MSH in a fresh Ham's F-12 medium and (iii) that containing no additive. After completion of the culture followed by fixation with 10% formalin, specimens were prepared by an ordinary method. The eumelanin (black melanin) production at the hair follicles was observed with a microscope. The results are shown in Table 3.

TABLE 3

| Specimen (No. in Table 1) | Eumelanin production | | |
|---|---|---|---|
| | Control (free from α-MSH) | $10^{-9}$M of α-MSH added | $10^{-9}$M of α-MSH and $10^{-8}$M of specimen added |
| 14 | ± | + | ± |
| 40 | ± | + | ± |
| 74 | ± | + | ± |
| 85 | ± | + | ± |

± weak
+ strong

It is apparent from the results shown in Table 3 that when α-MSH was used, a remarkable eumelanin production was recognized, while only slight eumelanin production was peculiar to the yellow mice in the control group (without additives). However, when the compound of the present invention was added in combination with α-MSH, the eumelanin production was only weak as in the control.

These results indicate that the compound of the present invention acted as an antagonist against α-MSH to strongly inhibit the melanin formation which is accelerated by α-MSH.

EXAMPLE 3

Components 1 to 7 shown in Table 4 were mixed together to obtain a solution and separately components 8 to 11 shown in the same Table were also mixed together to obtain another solution. The former solution was added to the latter solution under stirring to obtain an emulsion. Component 12 was added to the emulsion in the course of cooling it to room temperature to obtain a cream having a composition shown in Table 4, wherein the amounts are given in terms of wt. % (the same shall apply hereinafter).

TABLE 4

| | Component | Present Invention | Comparative Example |
|---|---|---|---|
| 1 | Liquid paraffin (#70) | 4.0 | 4.0 |
| 2 | Squalane | 15.0 | 15.0 |
| 3 | Cetostearyl alcohol | 6.0 | 6.0 |
| 4 | Beeswax | 2.0 | 2.0 |
| 5 | Glyceryl monostearate | 2.0 | 2.0 |
| 6 | POE (20) Sorbitan monolaurate | 2.0 | 2.0 |
| 7 | Propylparaben | 0.1 | 0.1 |
| 8 | Compound No. 40 in Table 1 | 0.001 | — |
| 9 | Diglycerol | 5.0 | 5.0 |
| 10 | Methylparaben | 0.2 | 0.2 |
| 11 | Purified water | balance | balance |
| 12 | Perfume | small amount | small amount |

The cream thus prepared was applied to pigmented spots (chloasmata or freckles) of eight male and female patients twice a day (in the morning and evening) for two months. As a result, the pigmented spots to which the cream containing the active component of the present invention had been applied were far more faded than those to which the comparative cream was applied. During or after the use of the cream for two months, no skin trouble was observed.

EXAMPLE 4

Components 1 to 7 shown in Table 5 were heated at 70° C. to obtain a solution. Separately, components 8 to 13 were heated at 70° C. to obtain another solution. The oil solution comprising the components 1 to 7 was added to the latter solution to obtain an emulsion. Component 14 was added to the emulsion in the course of cooling it to room temperature to obtain a milky lotion having a composition shown in Table 5.

TABLE 5

| | Component | Amount (%) |
|---|---|---|
| 1 | Liquid paraffin (#70) | 11.0 |
| 2 | Isopropyl myristate | 1.5 |
| 3 | Glyceryl monostearate | 0.5 |
| 4 | Stearic acid | 2.0 |
| 5 | POE (20) stearyl ether | 0.7 |
| 6 | Glycyrrhetinic acid | 0.1 |
| 7 | Butylparaben | 0.1 |
| 8 | Compound No. 26 in Table 1 | 0.0001 |
| 9 | Glycerol | 2.0 |
| 10 | Carbopol 941* | 0.1 |
| 11 | Ethanol | 10.0 |
| 12 | Methylparaben | 0.1 |
| 13 | Purified water | balance |
| 14 | Perfume | small amount |

*Carboxyvinyl polymer having a molecular weight of 1,000,000 to 1,500,000

EXAMPLE 5

A solution comprising components 1 to 4 shown in Table 6 and another solution comprising components 5 to 9 were prepared separately from each other. They were mixed together to prepare a beauty essence.

TABLE 6

| | Component | Amount (%) |
|---|---|---|
| 1 | Compound No. 14 in Table 1 | 0.01 |
| 2 | Glycerol | 4.0 |
| 3 | Carboxyvinyl polymer | 0.5 |

TABLE 6-continued

| | Component | Amount (%) |
|---|---|---|
| 4 | Purified water | balance |
| 5 | dl-α-Tocopherol acetate | 0.2 |
| 6 | Ethanol | 10.0 |
| 7 | Polyoxyethylene (40) hydrogenated castor oil | 0.5 |
| 8 | Methylparaben | 0.1 |
| 9 | Perfume | small amount |

EXAMPLE 6

A cream was prepared in the same manner as that of Example 3 except that the compound No. 40 shown in Table 1 was replaced with compound No. 37, 38, 39, 41, 46, 47, 82, 83, 84, 85 or 86 in Table 1.

Having evaluated the properties of a cream (present invention) containing Compound No. 85 set out in Table 1 and a cream (comparative example) free from the same by the same method as that of Example 3, it was clearly observed that the present invention relieved the pigmented spots.

EXAMPLE 7

A milky lotion was prepared in the same manner as that of Example 4 except that the compound No. 26 shown in Table 1 was replaced with compound No. 20, 23, 29, 77 or 80 in Table 1.

EXAMPLE 8

A beauty essence was prepared in the same manner as that of Example 5 except that the compound No. 14 shown in Table 1 was replaced with compound No. 8, 11, 15, 17, 74 or 75 in Table 1.

EXAMPLE 9

Compound Nos. 113 and 132 in Table 2 which were the active components of the present invention were synthesized by the solid phase method and purified as described below.

Arg which was the amino acid at the C-terminal was coupled with a crosslinked polystyrene resin. Then amino acids having the amino group protected with t-butoxycarbonyl group were coupled with the N-terminal one by one. After all the amino acids had been coupled with the resin, the peptide with the protective group was removed from the resin, and the protective group was removed.

The purified compound thus obtained was purified according to liquid chromatography to obtain the active components of the present invention (Compound Nos. 113 and 132 in Table 2).

EXAMPLE 10

MSH-inhibiting effects of the compounds of the present invention obtained in Example 9 (compound Nos. 113 and 132 in Table 2) and compounds of the present invention synthesized in the same manner as that of Example 9 (compound Nos. 116 and 135 in Table 2) were examined as described below.

Skin grafts (about 1 mm × 1 mm) of yellow mice (C 57 BL/6J-A') (7.5 days after the birth) containing hair follicle melanocytes were cultured in Ham's F-12 culture medium at 37° C. for 2 days. The culture media used were: (i) Ham's F-12 medium containing α-MSH, (ii) that containing both α-MSH and the compound of the present invention, i.e., α-MSH and the compound of the present invention were mixed so as to interact each other and then the skin grafts were added thereto, and (iii) that containing no additive. After completion of the culture followed by fixation with 10% formalin, specimens were prepared by an ordinary method. The eumelanin production at the hair follicles was observed with a microscope. The results are shown in Table 7.

TABLE 7

| | Eumelanin production | | |
|---|---|---|---|
| Specimen (No. in Table 2) | Control (free from α-MSH) | $10^{-9}$M of α-MSH added | $10^{-9}$M of α-MSH and $10^{-8}$M of specimen added |
| 113 | ± | + | ± |
| 116 | ± | + | ± |
| 132 | ± | + | ± |
| 135 | ± | + | ± |

±: weak
+: strong

It is apparent from the results shown in Table 7 that when α-MSH was used, a remarkable eumelanin production was recognized, while only slight eumelanin production was peculiarly to the yellow mice in the control group (without additives). However, when the compound of the present invention was added in combination with α-MSH, the eumelanin production was only weak similarly to that in the control.

These results indicate that the compound of the present invention acted as an inhibitor against α-MSH to strongly inhibit the melanin formation which is accelerated by α-MSH.

EXAMPLE 11

Components 1 to 7 shown in Table 8 were mixed together to obtain a solution and separately components 8 to 12 shown in the same Table were also mixed together to obtain another solution. The former solution was added to the latter solution under stirring to obtain an emulsion. Component 13 was added to the emulsion in the course of cooling it to room temperature to obtain a cream having a composition shown in Table 8, wherein the amounts are given in terms of wt. % (the same shall apply hereinafter).

TABLE 8

| | Component | Present invention | Present invention | Comparative example |
|---|---|---|---|---|
| 1 | Liquid paraffin (#70) | 5.0 | 5.0 | 5.0 |
| 2 | Squalane | 15.0 | 15.0 | 15.0 |
| 3 | Cetostearyl alcohol | 5.0 | 5.0 | 5.0 |
| 4 | Beeswax | 2.0 | 2.0 | 2.0 |
| 5 | Glyceryl monostearate | 2.0 | 2.0 | 2.0 |
| 6 | POE (20) Sorbitan monolaurate | 2.0 | 2.0 | 2.0 |
| 7 | Propylparaben | 0.1 | 0.1 | 0.1 |
| 8 | Compound No. 113 in Table 2 | 0.001 | — | — |
| 9 | Compound No. 132 in Table 2 | — | 0.001 | — |
| 10 | Diglycerol | 5.0 | 5.0 | 5.0 |
| 11 | Methylparaben | 0.1 | 0.1 | 0.1 |
| 12 | Purified water | balance | balance | balance |
| 13 | Perfume | small amount | small amount | small amount |

The cream thus prepared was applied to pigmented spots (chloasmata or freckles) of eight male and female patients twice a day (in the morning and evening) for two months. As a result, the pigmented spots to which the cream containing the Active Component No. 113 or 132 of the present invention had been applied were far more faded than those to which the comparative cream was applied. During or after the use of the cream for two months, no skin trouble was observed.

EXAMPLE 12

Components 1 to 7 shown in Table 9 were heated at 70° C. to obtain a solution. Separately, components 8 to 13 were heated at 70° C. to obtain another solution. The oil solution comprising the Components 1 to 7 was added to the latter solution to obtain an emulsion. Component 14 was added to the emulsion in the course of cooling it to room temperature to obtain a milky lotion having a composition shown in Table 9.

TABLE 9

| | Component | Amount (%) |
|---|---|---|
| 1 | Liquid paraffin (#70) | 10.0 |
| 2 | Isopropyl myristate | 2.0 |
| 3 | Glyceryl monostearate | 0.5 |
| 4 | Stearic acid | 2.0 |
| 5 | POE (20) stearyl ether | 1.0 |
| 6 | Glycyrrhetinic acid | 0.1 |
| 7 | Butylparaben | 0.1 |
| 8 | Compound No. 116 in Table 2 | 0.0001 |
| 9 | Glycerol | 2.0 |
| 10 | Carbopol 941* | 0.1 |
| 11 | Ethanol | 10.0 |
| 12 | Methylparaben | 0.1 |
| 13 | Purified water | balance |
| 14 | Perfume | small amount |

*Carboxyvinyl polymer having a molecular weight of 1,000,000 to 1,500,000

Having evaluated the milky lotion (present invention) set out in Table 9 and a milky lotion (comparative example) free from compound No. 116 by the same method as that of Example 3, it was clearly observed that the present invention relieved the pigmented spots.

EXAMPLE 13

A solution comprising components 1 to 4 shown in Table 10 and another solution comprising components 5 to 9 were prepared separately from each other. They were mixed together to prepare a beauty essence.

TABLE 10

| | Component | Amount (%) |
|---|---|---|
| 1 | Compound No. 135 in Table 2 | 0.01 |
| 2 | Glycerol | 5.0 |
| 3 | Carboxyvinyl polymer | 0.5 |
| 4 | Purified water | balance |
| 5 | dl-α-Tocopherol acetate | 0.1 |
| 6 | Ethanol | 10.0 |
| 7 | Polyoxyethylene (40) hydrogenated castor oil | 0.8 |
| 8 | Methylparaben | 0.1 |
| 9 | Perfume | small amount |

EXAMPLE 14

A milky lotion was prepared in the same manner as that of Example 12 except that the Compound No. 116 shown in Table 2 was replaced with Compound No. 114 or 115 in Table 2.

EXAMPLE 15

A beauty essence was prepared in the same manner as that of Example 13 except that the Compound No. 135 shown in Table 2 was replaced with Compound No. 133 or 134 in Table 2.

EXAMPLE 16

A cream was prepared in the same manner as that of Example 11 except that the Compound No. 113 or 132 in Table 2 was replaced with Compound No. 102, 107, 120, 124, 128, 137 or 139 shown in Table 2.

What is claimed is:

1. A melanocyte-stimulating hormone inhibitor consisting essentially of an amino acid sequence represented by the following general formula (IV), (V) or (VI):

X-His-Ser-Arg-Trp-Y     (IV)

P-Trp-Arg-Ser-His-Q     (V)

$X_1$-Leu-Ala-Cys-Ala-Arg-$Y_1$     (VI)

wherein His, Ser, Arg, Trp, Leu, Ala and Cys represent L- or D-histidine, serine, arginine, tryptophan, leucine, alanine and cysteine residues, respectively, X and P each represent a hydrogen, an acyl group having 1 to 12 carbon atoms, an amino acid residue, or acylated derivative thereof having 1 to 12 carbon atoms, peptide residue having 2 to 40 amino acid residues or acylated derivative thereof, and Y and Q each represent a hydroxyl group, an amino group, an amino acid residue, or amidated derivative thereof, or a peptide residue having 2 to 40 amino acid residues or amidated derivative thereof, and $X_1$ represents a hydrogen, an acyl group having 1 to 12 carbon atoms, an amino acid residue, or acylated derivative thereof having 1 to 12 carbon atoms, or a peptide residue having 2 to 40 amino acid residues or acylated derivative thereof, and $Y_1$ represents a hydroxyl group, an amino group, an amino acid residue, or amidated derivative thereof, or a peptide residue having 2 to 36 amino acid residues or amidated derivative thereof and wherein the peptide of the formula (IV) or (V) has a molecular weight in the range of 584 to 10,000 and the peptide of the formula (VI) has a molecular weight in the range of 532 to 10,000.

2. The inhibitor according to claim 1, wherein X and P each represent an acyl group, an acylated derivative of an amino acid residue or an acylated derivative of a peptide residue having 2 to 40 amino acid residues, and Y and Q each represent an amino group, an amidated amino acid residue or an amidated derivative of a peptide residue having 2 to 40 amino acid residues.

3. The inhibitor according to claim 1, wherein $X_1$ represents a hydrogen, an acyl group, or a peptide residue having an amino acid sequence of -Ile-Leu- or -Leu-His-Ala-Leu-Gln-Leu-Leu-Leu-Ile-Leu or acylated derivative thereof, and $Y_1$ represents a hydroxyl group, an amino group, or a peptide residue having an amino acid sequence of -Ile-Ser-Pro-Gly-Arg-Arg- or an amidated derivative thereof.

4. The inhibitor according to claim 1, wherein the peptide of the formula [IV] or [V] has a molecular weight in the range of 600 to 3,000.

5. The inhibitor according to claim 1, wherein the peptide of the formula [VI] has a molecular weight in the range of 532 to 4,000.

6. The inhibitor according to claim 1, wherein the inhibitor is a peptide of formula [IV] or [V] wherein X and P each represent an acyl group having 1 to 6 carbon atoms, an acylated derivative of an amino acid residue having 1 to 6 carbon atoms or an acylated derivative of a peptide residue having 2 to 20 amino acid residues, and Y and Q each represent an amino group, an amidated amino acid residue or an amidated derivative of a peptide residue having 2 to 20 amino acid residues.

7. The inhibitor according to claim 1 wherein the inhibitor is a peptide of the formula [VI] wherein $X_1$ represents a hydrogen, an acyl group having 1 to 6 carbon atoms, or a peptide residue having an amino acid sequence of -Ile-Leu- or -Leu-His-Ala-Leu-Gln-Leu-Leu-Leu-Ile-Leu or an acylated derivative thereof, and $Y_1$ represents a hydroxyl group, an amino group, or a peptide residue having an amino acid sequence of -Ile-Ser-Pro-Gly-Arg-Arg-or amidated derivative thereof.

8. A topical composition to inhibit melanocyte-stimulating hormone comprising an effective amount of a peptide of the following formula [I], [II], or [III] to inhibit melanocyte stimulating hormone:

-His-Ser-Arg-Trp-            [I]

-Trp-Arg-Ser-His            [II]

-Leu-Ala-Cys-Ala-Arg-            [III]

wherein His, Ser, Arg, Trp, Leu, Ala and Cys represent L- or D-histidine, serine, arginine, tryptophan, leucine, alanine and cysteine residues, respectively, and an inert carrier.

9. A topical composition to inhibit melanocyte-stimulating hormone comprising an effective amount of an amino acid sequence represented by the following general formula (IV), (V) or (VI) to inhibit melanocyte stimulating hormone:

X-His-Ser-Arg-Trp-Y            (IV)

P-Trp-Arg-Ser-His-Q            (V)

$X_1$-Leu-Ala-Cys-Ala-Arg-Y            (VI)

wherein His, Ser, Arg, Trp, Leu, Ala and Cys represent L- or D-histidine, serine, arginine, tryptophan, leucine, alanine and histidine, serine, arginine, tryptophan, leucine, alanine and cysteine residues, respectively, X and P each represent a hydrogen, an acyl group having 1 to 12 carbon atoms, an amino acid residue, or acylated derivative thereof having 1 to 12 carbon atoms, peptide residue having 2 to 40 amino acid residues or acylated derivative thereof, and Y and Q each represent a hydroxyl group, an amino group, an amino acid residue, or amidated derivative thereof, and or a peptide residue having 2 to 40 amino acid residues or amidated derivative thereof, and $X_1$ represents a hydrogen, an acyl group having 1 to 12 carbon atoms, an amino acid residue, or acylated derivative thereof having 1 to 12 carbon atoms, or a peptide residue having 2 to 40 amino acid residues or acylated derivative thereof, and $Y_1$, represents a hydroxyl group, an amino group, an amino acid residue, or amidated derivative thereof, or a peptide residue having 2 to 36 amino acid residue or amidated derivative thereof, wherein the peptide of the formula (IV) or (V) has a molecular weight in the range of 584 to 10,000 and the peptide of the formula (VI) has a molecular weight in the range of 532 to 10,000, and an inert carrier.

10. The composition according to claims 8 which contains 0.0000000001 to 1 wt. % of the protein.

11. The composition according to claims 9 which contains 0.0000000001 to 1 wt. % of the protein.

12. The composition according to claim 8 which contains 0.05 to 8 wt. % of a surfactant.

13. The composition according to claim 9 which contains 0.05 to 8 wt. % of a surfactant.

14. The composition according to claim 8 which contains 1 to 15 wt. % of a humectant.

15. The composition according to claim 9 which contains 1 to 15 wt. % of a humectant.

16. The composition according to claim 8, wherein the inert carrier is water.

17. The composition according to claim 9, wherein the inert carrier is water.

18. A method for inhibiting the function of melanocyte-stimulating hormone by topically applying a composition containing an effective amount of a peptide of the formula [I], [II] or [III] set forth in claim 8 to inhibit melanocyte-stimulating hormone.

19. A method for inhibiting the function of melanocyte-stimulating hormone by topically applying a composition containing an effective amount of a peptide of the formula [IV], [V] or [VI] set forth in claim 9 to inhibit melanocyte-stimulating hormone.

20. The melanocyte-stimulating hormone inhibitor according to claim 1 wherein the compound of general formula [IV] is selected from the following group:
H-His-Ser-Arg-Trp-OH,
Ac-His-Ser-Arg-Trp-NH$_2$,
Ac-His-D-Ser-Arg-Trp-NH$_2$,
H-Glu-His-Ser-Arg-Trp-Gly-OH,
Ac-Glu-His-Ser-Arg-Trp-Gly-NH$_2$,
Ac-Glu-His-D-Ser-Arg-Trp-Gly-NH$_2$,
H-Met-Glu-His-Ser-Arg-Trp-Gly-OH,
Ac-Met-Glu-His-Ser-Arg-Trp-Gly-NH$_2$,
Ac-Met-Glu-His-D-Ser-Arg-Trp-Gly-NH$_2$,
H-Nle-Glu-His-Ser-Arg-Trp-Gly-OH,
Ac-Nle-Glu-His-Ser-Arg-Trp-Gly-NH$_2$,
Ac-Nle-Glu-His-D-Ser-Arg-Trp-Gly-NH$_2$,
H-Met-Glu-His-Ser-Arg-Trp-Gly-Lys-OH,
Ac-Met-Glu-His-Ser-Arg-Trp-Gly-Lys-NH$_2$,
Ac-Met-Glu-His-D-Ser-Arg-Trp-Gly-Lys-NH$_2$,
H-Nle-Glu-His-Ser-Arg-Trp-Gly-Lys-OH,
Ac-Nle-Glu-His-Ser-Arg-Trp-Gly-Lys-NH$_2$,
Ac-Nle-Glu-His-D-Ser-Arg-Trp-Gly-Lys-NH$_2$,
H-Ser-Met-Glu-His-Ser-Arg-Trp-Gly-Lys-Pro-OH,
Ac-Ser-Met-Glu-His-Ser-Arg-Trp-Gly-Lys-Pro-NH$_2$,
Ac-Ser-Met-Glu-His-D-Ser-Arg-Trp-Gly-Lys-Pro-NH$_2$,
H-Ser-Nle-Glu-His-Ser-Arg-Trp-Gly-Lys-Pro-OH,
Ac-Ser-Nle-Glu-His-Ser-Arg-Trp-Gly-Lys-Pro-NH$_2$,
Ac-Ser-Nle-Glu-His-D-Ser-Arg-Trp-Gly-Lys-Pro-NH$_2$,
H-Ser-Tyr-Ser-Met-Glu-His-Ser-Arg-Trp-Gly-Lys-Pro-OH,
Ac-Ser-Tyr-Ser-Met-Glu-His-Ser-Arg-Trp-Gly-Lys-Pro-NH$_2$,
Ac-Ser-Tyr-Ser-Met-Glu-His-D-Ser-Arg-Trp-Gly-Lys-Pro-NH$_2$,
H-Ser-Tyr-Ser-Nle-Glu-His-Ser-Arg-Trp-Gly-Lys-Pro-OH,
Ac-Ser-Tyr-Ser-Nle-Glu-His-Ser-Arg-Trp-Gly-Lys-Pro-NH$_2$,
Ac-Ser-Tyr-Ser-Nle-Glu-His-D-Ser-Arg-Trp-Gly-Lys-Pro-NH$_2$,
H-D-Ser-Tyr-Ser-Met-Glu-His-Ser-Arg-Trp-Gly-Lys-Pro-OH,
Ac-D-Ser-Tyr-Ser-Met-Glu-His-Ser-Arg-Trp-Gly-Lys-Pro-NH$_2$,
Ac-D-Ser-Tyr-Ser-Met-Glu-His-D-Ser-Arg-Trp-Gly-Lys-Pro-NH$_2$,
H-D-Ser-Tyr-Ser-Nle-Gly-His-Ser-Arg-Trp-Gly-Lys-Pro-OH, Ac-D-Ser-Tyr-Ser-Nle-Glu-His-Ser-Arg-Trp-Gly-Lys-Pro-NH$_2$,
Ac-D-Ser-Tyr-Ser-Nle-Glu-His-D-Ser-Arg-Trp-Gly-Lys-Pro-NH$_2$,
H-Ser-Tyr-Ser-Met-Glu-His-Ser-Arg-Trp-Gly-Lys-Pro-Val-OH,
Ac-Ser-Tyr-Ser-Met-Glu-His-Ser-Arg-Trp-Gly-Lys-Pro-Val-OH,
H-Ser-Tyr-Ser-Met-Glu-His-Ser-Arg-Trp-Gly-Lys-Pro-Val-NH$_2$,
Ac-Ser-Tyr-Ser-Met-Glu-His-Ser-Arg-Trp-Gly-Lys-Pro-Val-NH$_2$,
Ac-Ser-Tyr-Ser-Met-Glu-His-D-Ser-Arg-Trp-Gly-Lys-Pro-Val-NH$_2$,
Bu-Ser-Tyr-Ser-Met-Glu-His-Ser-Arg-Trp-Gly-Lys-Pro-Val-NH$_2$,
H-Ser-Tyr-Ser-Nle-Glu-His-Ser-Arg-Trp-Gly-Lys-Pro-Val-OH,
Ac-Ser-Tyr-Ser-Nle-Glu-His-Ser-Arg-Trp-Gly-Lys-Pro-Val-OH,
H-Ser-Tyr-Ser-Nle-Glu-His-Ser-Arg-Trp-Gly-Lys-Pro-Val-NH$_2$,
Ac-Ser-Tyr-Ser-Nle-Glu-His-Ser-Arg-Trp-Gly-Lys-Pro-Val-NH$_2$,
Ac-Ser-Tyr-Ser-Nle-Glu-His-D-Ser-Arg-Trp-Gly-Lys-Pro-Val-NH$_2$,
Bu-Ser-Tyr-Ser-Nle-Glu-His-Ser-Arg-Trp-Gly-Lys-Pro-Val-NH$_2$,
H-D-Ser-Tyr-Ser-Met-Glu-His-Ser-Arg-Trp-Gly-Lys-Pro-Val-OH,
Ac-D-Ser-Tyr-Ser-Met-Glu-His-Ser-Arg-Trp-Gly-Lys-Pro-Val-NH$_2$,
Ac-D-Ser-Tyr-Ser-Met-Glu-His-D-Ser-Arg-Trp-Gly-Lys-Pro-Val-NH$_2$,
H-Ser-Tyr-Ser-Met-Glu-His-Ser-Arg-Trp-Gly-Lys-Pro-Nva-OH,
Ac-Ser-Tyr-Ser-Met-Glu-His-Ser-Arg-Trp-Gly-Lys-Pro-Nva-NH$_2$,
Ac-Ser-Tyr-Ser-Met-Glu-His-D-Ser-Arg-Trp-Gly-Lys-Pro-Nva-NH$_2$,
H-Ser-Tyr-Ser-Met-Glu-His-Ser-Arg-Trp-Gly-Lys-Pro-Met-OH,
Ac-Ser-Tyr-Ser-Met-Glu-His-Ser-Arg-Trp-Gly-Lys-Pro-Met-NH$_2$,
Ac-Ser-Tyr-Ser-Met-Glu-His-D-Ser-Arg-Trp-Gly-Lys-Pro-Met-NH$_2$,
H-D-Ser-Tyr-Ser-Nle-Glu-His-Ser-Arg-Trp-Gly-Lys-Pro-Val-OH,
Ac-D-Ser-Tyr-Ser-Nle-Glu-His-Ser-Arg-Trp-Gly-Lys-Pro-Val-NH$_2$,
Ac-D-Ser-Tyr-Ser-Nle-Glu-His-D-Ser-Arg-Trp-Gly-Lys-Pro-Val-NH$_2$,
H-Ser-Tyr-Phe-Met-Glu-His-Ser-Arg-Trp-Gly-Lys-Pro-Val-OH,
Ac-Ser-Tyr-Phe-Met-Glu-His-Ser-Arg-Trp-Gly-Lys-Pro-Val-NH$_2$ and
Ac-Ser-Tyr-Phe-Met-Glu-His-D-Ser-Arg-Trp-Gly-Lys-Pro-Val-NH$_2$.

21. The melanocyte-stimulating hormone inhibitor according to claim 1 wherein the compound of general formula [V] is selected from the following group:
H-Trp-Arg-Ser-His-OH,
Ac-Trp-Arg-D-Ser-His-NH$_2$,
Ac-Trp-Arg-D-Ser-His-NH$_2$,
H-Cys-Trp-Arg-Ser-His-Gln-OH,
Ac-Cys-Trp-Arg-Ser-His-Gln-NH$_2$,
Ac-Cys-Trp-Arg-D-Ser-His-Gln-NH$_2$,
H-Cys-Trp-Arg-Ser-His-Gln-Pro-OH,
Ac-Cys-Trp-Arg-Ser-His-Gln-Pro-NH$_2$,
Ac-Cys-Trp-Arg-D-Ser-His-Gln-Pro-NH$_2$,
H-Cys-Cys-Trp-Arg-Ser-His-Gln-Pro-NH$_2$,
Ac-Cys-Cys-Trp-Arg-Ser-His-Gln-Pro-NH$_2$,
Ac-Cys-Cys-Trp-Arg-D-Ser-His-Gln-Pro-NH$_2$,
H-His-Cys-Cys-Trp-Arg-Ser-His-Gln-Pro-Ala-OH,
Ac-His-Cys-Cys-Trp-Arg-Ser-His-Gln-Pro-Ala-NH$_2$,
Ac-His-Cys-Cys-Trp-Arg-D-Ser-His-Gln-Pro-Ala-NH$_2$,
H-His-Cys-Cys-Trp-Arg-Ser-His-Gln-Pro-Ala-Arg-Pro-OH,
Ac-His-Cys-Cys-Trp-Arg-Ser-His-Gln-Pro-Ala-Arg-Pro-NH$_2$,
Ac-His-Cys-Cys-Trp-Arg-D-Ser-His-Gln-Pro-Ala-Arg-Pro-NH$_2$,
H-Cys-His-Cys-Cys-Trp-Arg-Ser-His-Gln-Pro-Ala-Arg-Pro-OH,
Ac-Cys-His-Cys-Cys-Trp-Arg-Ser-His-Gln-Pro-Ala-Arg-Pro-OH,
H-Cys-His-Cys-Cys-Trp-Arg-Ser-His-Gln-Pro-Ala-Arg-Pro-NH$_2$,
Ac-Cys-His-Cys-Cys-Trp-Arg-Ser-His-Gln-Pro-Ala-Arg-Pro-NH$_2$,
Ac-Cys-His-Cys-Cys-Trp-Arg-D-Ser-His-Gln-Pro-Ala-Arg-Pro-NH$_2$,
Bu-Cys-His-Cys-Cys-Trp-Arg-Ser-His-Gln-Pro-Ala-Arg-Pro-NH$_2$,
H-Leu-Met-Leu-Gly-Pro-Leu-Cys-His-Cys-Cys-Trp-Arg-Ser-His-Gln-Pro-Ala-Arg-Pro-Phe-Leu-Leu-Gly-Leu-OH,
Ac-Leu-Met-Leu-Gly-Pro-Leu-Cys-His-Cys-Cys-Trp-Arg-Ser-His-Gln-Pro-Ala-Arg-Pro-Phe-Leu-Leu-Gly-Leu-OH,
H-Leu-Met-Leu-Gly-Pro-Leu-Cys-His-Cys-Cys-Trp-Arg-Ser-His-Gln-Pro-Ala-Arg-Pro-Phe-Leu-Leu-Gly-Leu-NH$_2$,
Ac-Leu-Met-Leu-Gly-Pro-Leu-Cys-His-Cys-Cys-Trp-Arg-Ser-His-Gln-Pro-Ala-Arg-Pro-Phe-Leu-Leu-Gly-Leu-NH$_2$,
Ac-Leu-Met-Leu-Gly-Pro-Leu-Cys-His-Cys-Cys-Trp-Arg-D-Ser-His-Gln-Pro-Ala-Arg-Pro-Phe-Leu-Leu-Gly-Leu-NH$_2$ and
Bu-Leu-Met-Leu-Gly-Pro-Leu-Cys-His-Cys-Cys-Trp-Arg-Ser-His-Gln-Pro-Ala-Arg-Pro-Phe-Leu-Leu-Gly-Leu-NH$_2$.

22. The melanocyte-stimulating hormone inhibitor according to claim 1 wherein the compound of general formula [VI] s selected from the following group:
Leu-Ala-Cys-Ala-Arg
Ac-Leu-Ala-Cys-Ala-Arg-NH$_2$,
Leu-Ala-Cys-Ala-Arg-Ile,
Ac-Leu-Ala-Cys-Ala-Arg-Ile-NH$_2$,
Leu-Ala-Cys-Ala-Arg-Ile-Ser,
Ac-Leu-Ala-Cys-Ala-Arg-Ile-Ser-NH$_2$,
Leu-Ala-Cys-Ala-Arg-Ile-Ser-Pro,
Ac-Leu-Ala-Cys-Ala-Arg-Ile-Ser-Pro-NH$_2$,
Leu-Ala-Cys-Ala-Arg-Ile-Ser-Pro-Gly,
Ac-Leu-Ala-Cys-Ala-Arg-Ile-Ser-Pro-Gly-NH$_2$,
Leu-Leu-Ala-Cys-Ala-Arg-Ile-Ser-Pro-Gly-Arg,
Ac-Leu-Leu-Ala-Cys-Ala-Arg-Ile-Ser-Pro-Gly-Arg-NH$_2$,
Ile-Leu-Leu-Ala-Cys-Ala-Arg-Ile-Ser-Pro-Gly-Arg-Arg,
Ac-Ile-Leu-Leu-Ala-Cys-Ala-Arg-Ile-Ser-Pro-Gly-Arg-Arg,
Ile-Leu-Leu-Ala-Cys-Ala-Arg-Ile-Ser-Pro-Gly-Arg-Arg-NH$_2$, Ac-Ile-Leu-Leu-Ala-Cys-Ala-Arg-Ile-Ser-Pro-Gly-Arg-Arg-$NH_2$,
Bu-Ile-Leu-Leu-Ala-Cys-Ala-Arg-Ile-Ser-Pro-Gly-Arg-Arg-$NH_2$,
Leu-Ile-Leu-Leu-Ala-Cys-Ala-Arg-Ile-Ser-Pro-Gly-Arg-Arg,
Ac-Leu-Ile-Leu-Leu-Ala-Cys-Ala-Arg-Ile-Ser-Pro-Gly-Arg-Arg-$NH_2$,
Leu-Leu-Ile-Leu-Leu-Ala-Cys-Ala-Arg-Ile-Ser-Pro-Gly-Arg-Arg,
Ac-Leu-Leu-Ile-Leu-Leu-Ala-Cys-Ala-Arg-Ile-Ser-Pro-Gly-Arg-Arg-$NH_2$,
Leu-Leu-Leu-Ile-Leu-Leu-Ala-Cys-Ala-Arg-Ile-Ser-Pro-Gly-Arg-Arg,
Ac-Leu-Leu-Leu-Ile-Leu-Leu-Ala-Cys-Ala-Arg-Ile-Ser-Pro-Gly-Arg-Arg-$NH_2$,
Gln-Leu-Leu-Leu-Ile-Leu-Leu-Ala-Cys-Ala-Arg-Ile-Ser-Pro-Gly-Arg-Arg,
Ac-Gln-Leu-Leu-Leu-Ile-Leu-Leu-Ala-Cys-Ala-Arg-Ile-Ser-Pro-Gly-Arg-Arg-$NH_2$,
Leu-Gln-Leu-Leu-Leu-Ile-Leu-Leu-Ala-Cys-Ala-Arg-Ile-Ser-Pro-Gly-Arg-Arg,
Ac-Leu-Gln-Leu-Leu-Leu-Ile-Leu-Leu-Ala-Cys-Ala-Arg-Ile-Ser-Pro-Gly-Arg-Arg-$NH_2$,
Ala-Leu-Gln-Leu-Leu-Leu-Ile-Leu-Leu-Ala-Cys-Ala-Arg-Ile-Ser-Pro-Gly-Arg-Arg,
Ac-Ala-Leu-Gln-Leu-Leu-Leu-Ile-Leu-Leu-Ala-Cys-Ala-Arg-Ile-Ser-Pro-Gly-Arg-Arg-$NH_2$,
His-Ala-Leu-Gln-Leu-Leu-Leu-Ile-Leu-Leu-Ala-Cys-Ala-Arg-Ile-Ser-Pro-Gly-Arg-Arg,
Ac-His-Ala-Leu-Gln-Leu-Leu-Leu-Ile-Leu-Leu-Ala-Cys-Ala-Arg-Ile-Ser-Pro-Gly-Arg-Arg-$NH_2$
Leu-His-Ala-Leu-Gln-Leu-Leu-Leu-Ile-Leu-Leu-Ala-Cys-Ala-Arg-Ile-Ser-Pro-Gly-Arg-Arg,
Ac-Leu-His-Ala-Leu-Gln-Leu-Leu-Leu-Ile-Leu-Leu-Ala-Cys-Ala-Arg-Ile-Ser-Pro-Gly-Arg-Arg,
Leu-His-Ala-Leu-Gln-Leu-Leu-Leu-Ile-Leu-Leu-Ala-Cys-Ala-Arg-Ile-Ser-Pro-Gly-Arg-Arg-$NH_2$,
Ac-Leu-His-Ala-Leu-Gln-Leu-Leu-Leu-Ile-Leu-Leu-Ala-Cys-Ala-Arg-Ile-Ser-Pro-Gly-Arg-Arg-$NH_2$,
Bu-Leu-His-Ala-Leu-Gln-Leu-Leu-Leu-Ile-Leu-Leu-Ala-Cys-Ala-Arg-Ile-Ser-Pro-Gly-Arg-Arg-$NH_2$,
Leu-Asn-His-Leu-Gly-Leu-His-Ala-Leu-Gln-Leu-Leu-Leu-Ile-Leu-Leu-Ala-Cys-Ala-Arg-Ile-Ser-Pro-Gly-Arg-Arg-Ala-Cys-Arg-Pro-Cys,
Ac-Leu-Asn-His-Leu-Gly-Leu-His-Ala-Leu-Gln-Leu-Leu-Leu-Ile-Leu-Leu-Ala-Cys-Ala-Arg-Ile-Ser-Pro-Gly-Arg-Arg-Ala-Cys-Arg-Pro-Cys-$NH_2$,
Gln-Phe-Leu-Leu-Gln-Leu-Asn-His-Leu-Gly-Leu-His-Ala-Leu-Gln-Leu
-Leu-Leu-Ile-Leu-Leu-Ala-Cys-Ala-Arg-Ile-Ser-Pro-Gly-Arg-Arg-Ala-Cys-Arg-Pro-Cys-Pro-His-Ala-Val-Leu and
Ac-Gln-Phe-Leu-Leu-Gln-Leu-Asn-His-Leu-Gly-Leu-His-Ala-Leu-Gln-Leu-Leu-Leu-Ile-Leu-Leu-Ala-Cys-Ala-Arg-Ile-Ser-Pro-Gly-Arg-Arg-Ala-Cys-Arg-Pro-Cys-Pro-His-Ala-Val-Leu-$NH_2$.

23. A method for inhibiting the function of melanocyte-stimulating hormone by topically applying a composition containing an effective amount of a peptide of the [IV] formula as set forth in claim 20.

24. A method for inhibiting the function of melanocyte-stimulating hormone by topically applying a composition containing an effective amount of a peptide of the [V] formula as set forth in claim 21.

25. A method for inhibiting the function of melanocyte-stimulating hormone by topically applying a composition containing an effective amount of a peptide of the formula [VI] as set forth in claim 22.

* * * * *